United States Patent
Gordon et al.

(10) Patent No.: US 7,246,514 B2
(45) Date of Patent: Jul. 24, 2007

(54) METHOD FOR VERIFYING SENSORS INSTALLATION AND DETERMINING THE LOCATION OF THE SENSORS AFTER INSTALLATION IN A STRUCTURAL HEALTH MANAGEMENT SYSTEM

(75) Inventors: Grant A. Gordon, Peoria, AZ (US); Joseph Nutaro, Phoenix, AZ (US); Steven R. Thompson, Phoenix, AZ (US)

(73) Assignee: Honeywell International, Inc., Morristown, NJ (US)

( * ) Notice: Subject to any disclaimer, the term of this patent is extended or adjusted under 35 U.S.C. 154(b) by 263 days.

(21) Appl. No.: 10/976,725

(22) Filed: Oct. 29, 2004

(65) Prior Publication Data

US 2006/0095223 A1    May 4, 2006

(51) Int. Cl.
*G01M 1/14* (2006.01)
(52) U.S. Cl. ....................................................... 73/1.82
(58) Field of Classification Search .................. 73/1.82
See application file for complete search history.

(56) References Cited

U.S. PATENT DOCUMENTS

| | | |
|---|---|---|
| 4,419,900 A | 12/1983 | Scott et al. |
| 5,184,516 A | 2/1993 | Blazic et al. |
| 5,383,133 A | 1/1995 | Staple |
| 5,774,376 A | 6/1998 | Manning |
| 6,006,163 A | 12/1999 | Lichtenwalner et al. |
| 6,076,405 A | 6/2000 | Schoess |
| 6,192,759 B1 | 2/2001 | Schoess |
| 6,370,964 B1 | 4/2002 | Chang et al. |
| 6,396,262 B2 | 5/2002 | Light et al. |
| 7,006,944 B2 * | 2/2006 | Brand ........................ 702/150 |
| 2001/0022514 A1 | 9/2001 | Light et al. |
| 2001/0047691 A1 | 12/2001 | Dzenis |
| 2002/0154029 A1 | 10/2002 | Walters et al. |
| 2003/0009300 A1 | 1/2003 | Giurgiutiu |
| 2003/0167141 A1 | 9/2003 | Staszewski |
| 2003/0233876 A1 | 12/2003 | Huang et al. |
| 2005/0256689 A1 * | 11/2005 | Schulz ........................ 703/11 |

* cited by examiner

*Primary Examiner*—Robert Raevis
(74) *Attorney, Agent, or Firm*—Ingrassia Fisher & Lorenz (57) ABSTRACT

In the present invention, a method is provided for installing and locating a plurality of sensors distributed on a structure as part of a structural health monitoring system. The method includes verifying the proper installation of the plurality of sensors and determining the location of the plurality of sensors. In one aspect of the present invention, the step of verifying the proper installation further comprises verifying that each of the plurality of sensors are properly coupled to a sensor data collector and verifying that each of the plurality of sensors are installed in a proper location. In another aspect of the present invention, the step of determining the location of the plurality of sensors further comprises determining the positioning of each sensor in reference to fixed structures in the structure.

10 Claims, 7 Drawing Sheets

METHOD FOR VERIFYING SENSORS INSTALLATION AND DETERMINING THE LOCATION OF THE SENSORS AFTER INSTALLATION IN A STRUCTURAL HEALTH MANAGEMENT SYSTEM

TECHNICAL FIELD

This invention relates to the field of structural health management, and more specifically to a method for verifying sensor installation and determining the location of the sensors after installation in a structural health management system.

BACKGROUND

Nondestructive testing is a procedure for determining the quality or characteristics of a structure without permanently altering the structure or the structure's properties. Examples include ultrasonic and radiographic inspection. In the avionics field, nondestructive evaluations of airplane components are done to insure the structural integrity of the airplane. In typical airplane maintenance approaches, a certified inspector performs one or more nondestructive tests of the aircraft. This process may be repeated at regular intervals to monitor the structural health of the aircraft.

While this type of nondestructive testing scheme can be effective, it has several drawbacks. First, the test typically needs to be conducted by trained inspectors, which can incur significant costs, including the potential loss of operational revenue, when having an inspector perform the tests on site. Second, to enable efficient analysis and repetitive comparison over time, a non-subjective decision process driven by inspection data, inspection method parameters, location, decision criteria, and material properties within the context of the structure being inspected may be required. Current inspection approaches may not preserve these necessary components. Although each inspection can be analyzed individually, a collection of inspections may not be analyzed in toto.

To resolve some of the drawbacks of current nondestructive schemes, other structural health management schemes have been developed. In one structural health management technique, ultrasonic transducers can be placed, for example, on the fuselage of the aircraft to be tested. The ultrasonic transducers are then coupled to an onboard testing computer. The testing computer can be used to run nondestructive tests when needed by using the installed ultrasonic transducers.

The above-described system allows for nondestructive testing to be done without having an inspector bring equipment to the aircraft. Additionally, the automated inspection and determination of the state of the inspected material preserves accurate location data, as well as the associated data used to perform the inspection and make the determination. This allows multiple self-referential inspections of an area over an extended period of time, enabling correlation, trending and other sophisticated analysis of the inspection data across vehicles and over time.

However, in order to accurately interpret data produced from the system, the sensors must be correctly coupled to the system and must be placed in a proper location. Therefore, there is a need for a method and system for verifying sensor installation and determining the location of the sensors after installation in a structural health management system.

BRIEF SUMMARY

In the present invention, a method is provided for installing and locating a plurality of sensors distributed on a structure as part of a structural health monitoring system. The method includes verifying the proper installation of the plurality of sensors and determining the location of the plurality of sensors. In one aspect of the present invention, the step of verifying the proper installation further comprises verifying that each of the plurality of sensors are properly coupled to a sensor data collector and verifying that each of the plurality of sensors are installed in a proper location. In another aspect of the present invention, the step of determining the location of the plurality of sensors further comprises determining the positioning of each sensor in reference to known locations in the structure.

In another aspect of the present invention, a structural health monitoring system is disclosed. In one embodiment, the system comprises a plurality of sensors installed in a structure having local boundaries for each sensor and a processor coupled to each of the sensors. The processor is configured to determine a sensor time of flight between the sensors and a boundary time of flight between each sensor and the sensor's local boundaries. The processor is further configured to calculate an updated location for each of the sensors from the sensor time of flight and the boundary time of flight. The boundary time of flight and the sensor time of flight can be used to determine where the sensors are located.

In another embodiment the installation of the structural health monitoring system is verified by the system. The system comprises a plurality of sensors installed on a structure and a processor coupled to each of the sensors and operable to determine if each sensor is coupled to a data collector and if all sensors are properly installed within a predetermined location.

BRIEF DESCRIPTION OF THE DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. While the invention is discussed in an avionics embodiment, the teachings of the present invention are applicable to many different fields of endeavor.

Figure 1:
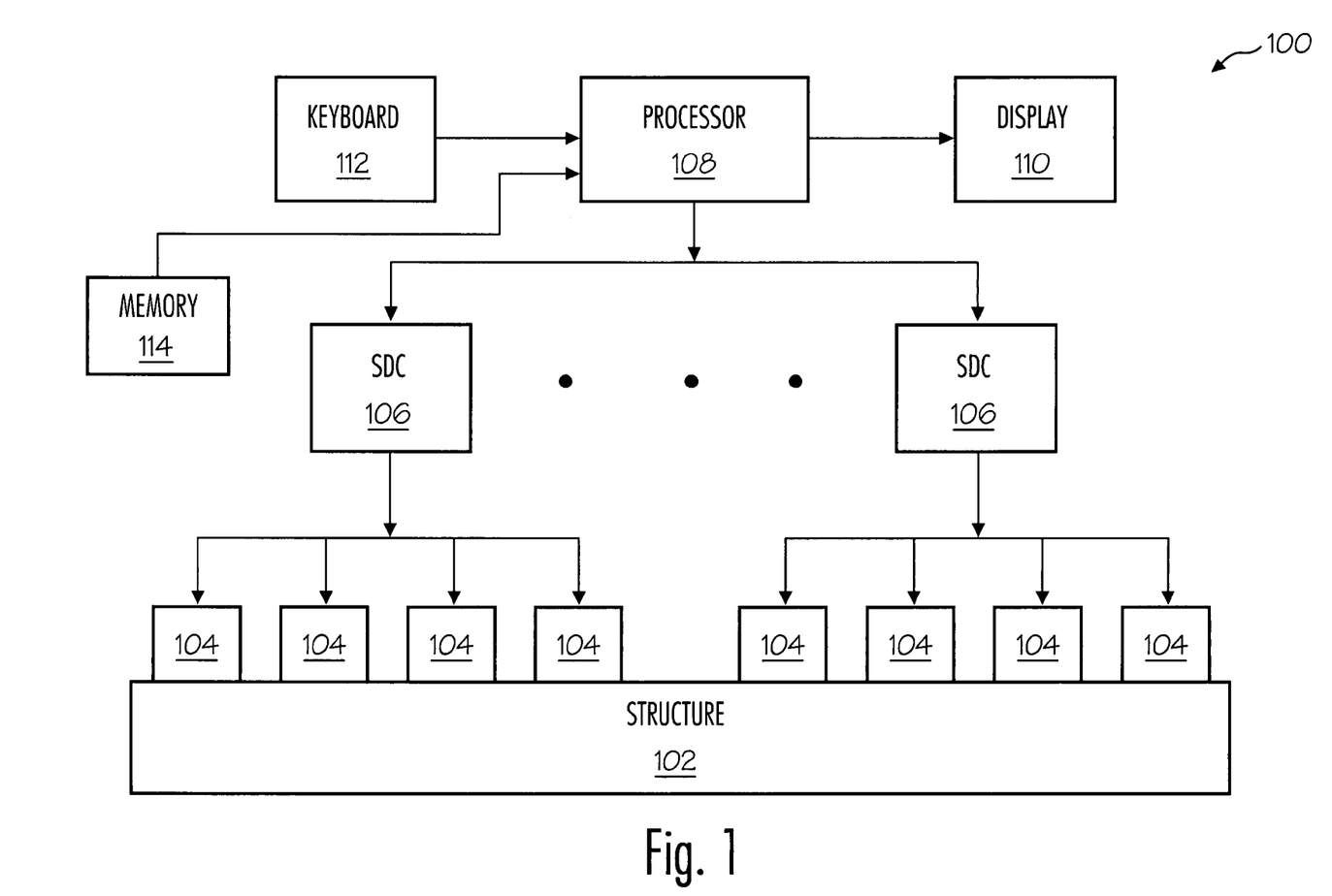
FIG. 1 illustrates an exemplary structural health mounting system in accordance with the teachings of the present invention.

FIG. 1 illustrates an exemplary structural health management system 100 in accordance with the teachings of the present invention. Structural health management system 100 includes a plurality of sensors 104 coupled to one or more sensor data collectors 106. Each sensor 104 is mounted to a structure 102 to be tested. The output of all the sensor data collectors 106 are provided as an input to at least one structural health monitoring processor 108. Various inputs and outputs can be provided to structural health monitoring processor 108. For example, processor 108 can be coupled to various input/output devices including a display 110, a keyboard 112 and the like. Processor 108 also is coupled to a memory 114.

Sensors 104 can be ultrasonic transducers that convert electrical signals into mechanical vibrations and mechanical vibrations into electrical signals. Typically, sensor 104 converts electricity into mechanical vibrations that propagate waves in the structure 102 to which the sensor 104 is coupled through elastic deformation (known as elastic waves). The propagated waves interact with various features within the structure 102 such as flaws or defects. The sensor 104 can receive transmitted and reflected waves and convert the mechanical vibrations caused by these waves into electrical signals. These electrical signals can then be analyzed to determine if there are any flaws or defects in the structure 102.

The amount of time it takes for a wave to travel between two sensed locations is known as the time-of-flight. In addition to the time-of-flight, signal amplitude, signal energy (area under the rectified voltage curve) and other features of an elastic wave received by sensor 104 can be used in models to predict the underlying damage state of the area traversed by the propagated elastic wave. Various features within the structure 102, such as fatigue cracks or other structural flaws, can be identified and located based on these values obtained from data collected by sensor 104 and others.

While many different designs for sensors 104 exist, in one embodiment, sensor 104 is a piezoelectric transducer. Piezoelectric transducers produce mechanical vibrations when an electric signal is applied and produce electrical signals when receiving mechanical vibrations. Typically, piezoelectric transducers use piezoelectric ceramics that can be engineered to produce different wave modes.

Different types of waves induced by piezoelectric transducers can be used in nondestructive testing. In an embodiment of the present invention, the sensors 104 produce Lamb waves in structure 102. Lamb waves propagate throughout the entire thickness of plate-like structures, such as the composite material used for the skin of an aircraft. Lamb waves are a form of guided elastic waves distinct from the bulk waves used in traditional ultrasonic inspections. Lamb waves traverse along the plate like structures while exciting material throughout the plate's thickness. As a consequence, the use of Lamb waves allows for distributed sensor schemes to examine the composite plate-like structure over a given area without the need to scan the transducers over certain areas.

Sensor data collectors (SDCs) 106, in one embodiment of the present invention, collect data from the sensors 104 in the form of electrical signals and send the data to processor 108 for evaluation. In another embodiment, sensor data collectors 106 collect data and can perform some analysis on the data prior to sending the data to the processor 108. By providing multiple sensor data collectors 106, if one sensor data collector 106 was to fail, the entire structural health management system 100 would not fail. Additionally, in one embodiment, SDCs 106 accept multiple sensor inputs and provide a single high speed data output, which results in a reduction in the amount of wiring required between the sensors 104 and the processor 108. While SDCs 106 are useful in reducing wiring and complexity, in one embodiment of the present invention, SDCs 106 are not used and data is routed from the sensors 104 to the processor 108.

Processor 108 can receive data collected from the sensors 104, either directly or via SDCs 106. Processor 108 can process data to determine the health of structure 102. Processor 108 can also support the execution of routines to verify the installation and determine the location of sensors. Processor 108 can be a commercial off the shelf processor and can include any components necessary to allow processor 108 to process the data. Processor 108 can couple to input/output devices such as the display 110, such as a CRT or LCD display, that displays information to a user.

Memory 114 can provide storage needed for programs executing on the processor 108. Also, memory 114 can provide storage of data used in the various routines executing on processor 108, including any needed databases, tables, listings and the like. Memory 114 can be any of numerous types of memory used with processor 108. While memory 114 is shown as a single box in FIG. 1, memory 114 can represent two or more distinct memories, such as random access memory (RAM) and magnetic storage, for example, a hard drive.

Structure 102 can be any one of numerous types of material of interest to be tested. In one embodiment, structure 102 is a composite material used for the skin of an aircraft. In one exemplary embodiment, structure 102 is a plate-like composite material such as the material used to form modern aircraft skin.

Figure 2:
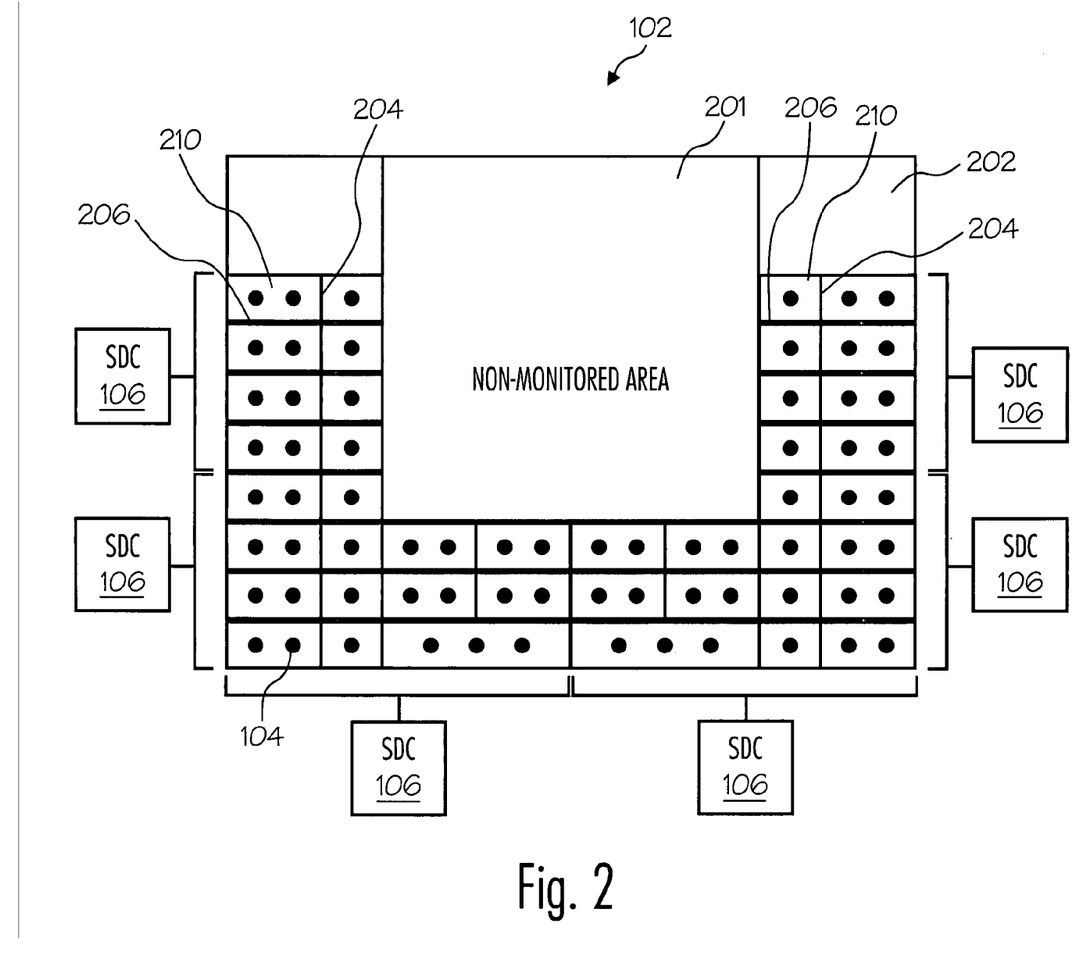
FIG. 2 illustrates the placement of sensors around a non-monitored section of an aircraft in accordance with the teachings of the present invention.

An exemplary arrangement of the sensors 104 and SDCs 106 in a structural health management system 100 is illustrated in FIG. 2. To avoid unnecessarily complicating FIG. 2, SDCs 106 are illustrated as associated with a grouping of sensors in FIG. 2. As better viewed in FIG. 1, each sensor 104 will be coupled to one of the SDCs 106. FIG. 2 illustrates an exemplary section of structure 102 to be tested. As shown in FIG. 2, one or more sensors 104 are placed on the inside surface 202 of the structure 102 in sections 210 bordered by a pair of stringer members 206 and a pair of frame members 204. In the embodiment of FIG. 2, the structure 102 is adjacent to a non-monitored area 201. Non-monitored area 201 can be any area not monitored by the system 100 and, in an avionics embodiment where the structure 102 is aircraft skin, the non-monitored area 201 can be a structure such as a window, door and the like. As noted, FIG. 2 illustrates the inside surface 202 of the structure 102; the outside of the structure 102 is not visible in this perspective.

In operation, each sensor 104 can produce, transmit and receive elastic wave energy. The elastic wave energy, produce by a sensor 104 converting mechanical energy to an elastic wave, can manifest itself in a variety of forms such as transient Lamb Waves, bulk waves, Rayleigh waves and the like. These elastic waves can be transmitted, reflected, refracted, mode converted and attenuated as the elastic waves propagate through out the structure, interacting with internal features. As discussed previously, characteristics of any defect can be determined, in part, from the time-of-flight, signal amplitude, and signal energy (area under the rectified voltage curve) of the propagated elastic waves as received by a sensor. Additionally, the time of flight between sensors or between the start of an elastic wave and its return from reflection of a boundary can be used to determine distances between sensors and between sensors and boundaries.

Of course, a key to a working structural health monitoring system, such as system 100 depicted in FIGS. 1-2, is the accurate placement of the sensors 104 when the sensors 104 are installed. Errors in the placement can occur in two ways. First, when one or more sensors 104 are initially installed or when one or more sensors 104 are replaced during maintenance, a sensor 104 might be connected incorrectly to the SDC 106 or the sensor 104 may be connected to the wrong SDC 106. Second, when the sensor 104 is placed on the structure 102, the sensors 104 may be installed outside of an acceptable installation location.

Figure 3:
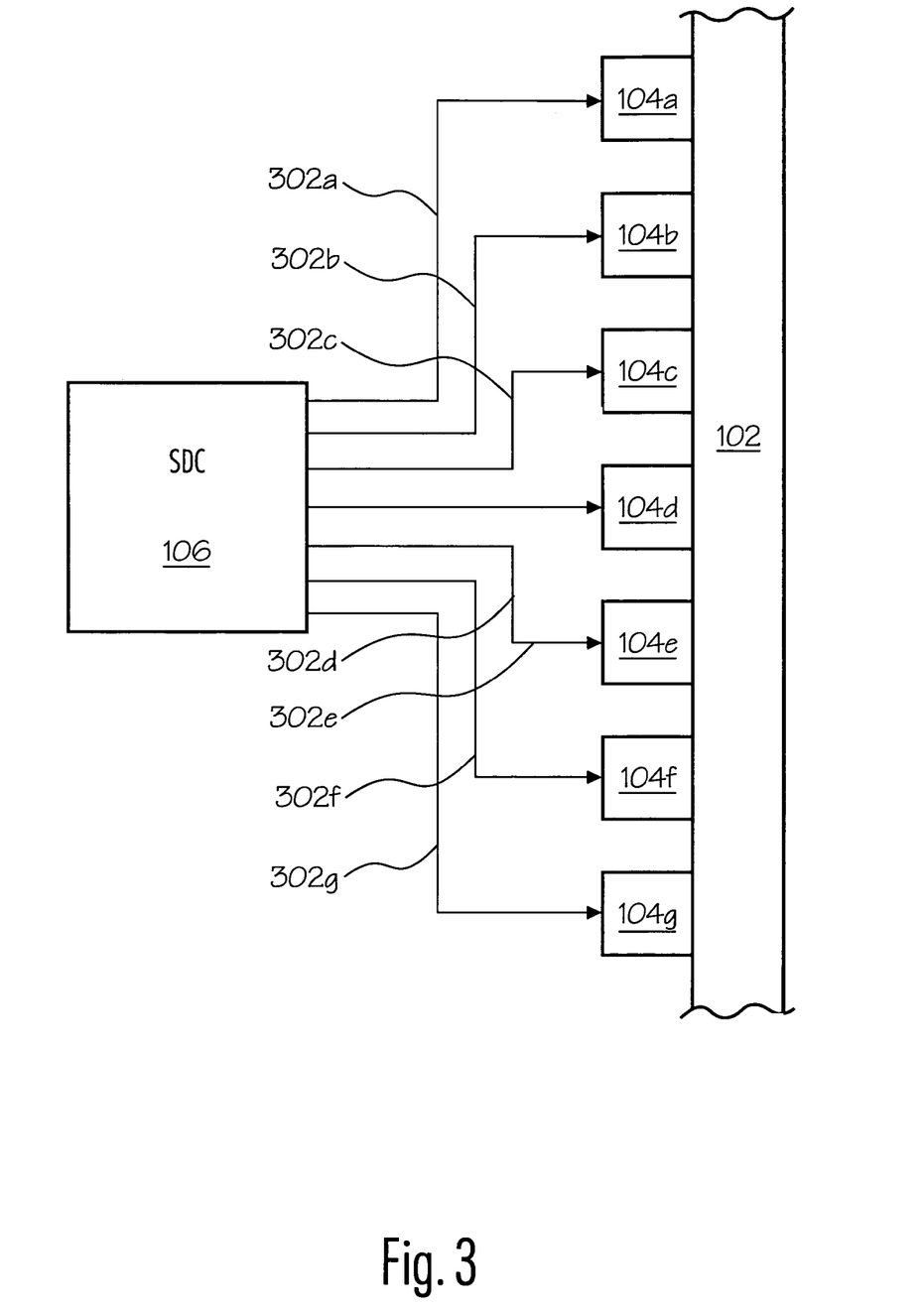
FIG. 3 illustrates an SDC connected to a plurality of sensors in accordance with the teachings of the present invention.

As illustrated in FIG. 1, each sensor 104 connects to a specific SDC 106. Further, each SDC 106, in one embodiment, connects to each of its sensors 104, in a specific way. For example, the SDC 106, in one embodiment, can include a number of separate ports with each port connected to a specific sensor 104. FIG. 3 is a block diagram illustrating such an arrangement. FIG. 3 includes a part of the structure 102 as shown in FIG. 2. In the exemplary embodiment of FIG. 3, the SDC 106 includes eight connections 302a-302g that couple the SDC 106 to each of eight sensors 104a-104g. In the exemplary arrangement of FIG. 3, connection 302a connects the SDC 106 to sensor 104a, connection 302b connects the SDC 106 to sensor 104b, connection 302c connects the SDC 106 to sensor 104c, connection 302d connects the SDC 106 to sensor 104d, connection 302e connects the SDC 106 to sensor 104e, connection 302f connects the SDC 106 to sensor 104f, connection 302g connects the SDC 106 to sensor 104g. By connecting specific ports to specific sensors, the system 100 can correctly control the correct sensor 104 to send a pulse when the system 100 is in operation. Also, the data collected at sensors 104 can be processed correctly if the system 100 correctly knows what sensor 104 is operating at a given location. While the embodiment of FIG. 3 shows multiple sensors 104 connected to a specific connection, other ways of connecting the sensors 104 to the SDC 106 that require the sensors 104 be connected in a structured manner are within the scope of the teachings of the present invention. Additionally, the number of sensors 104 that can couple to the SDC 106 can be varied based on systems needs or other factors.

Figure 4:
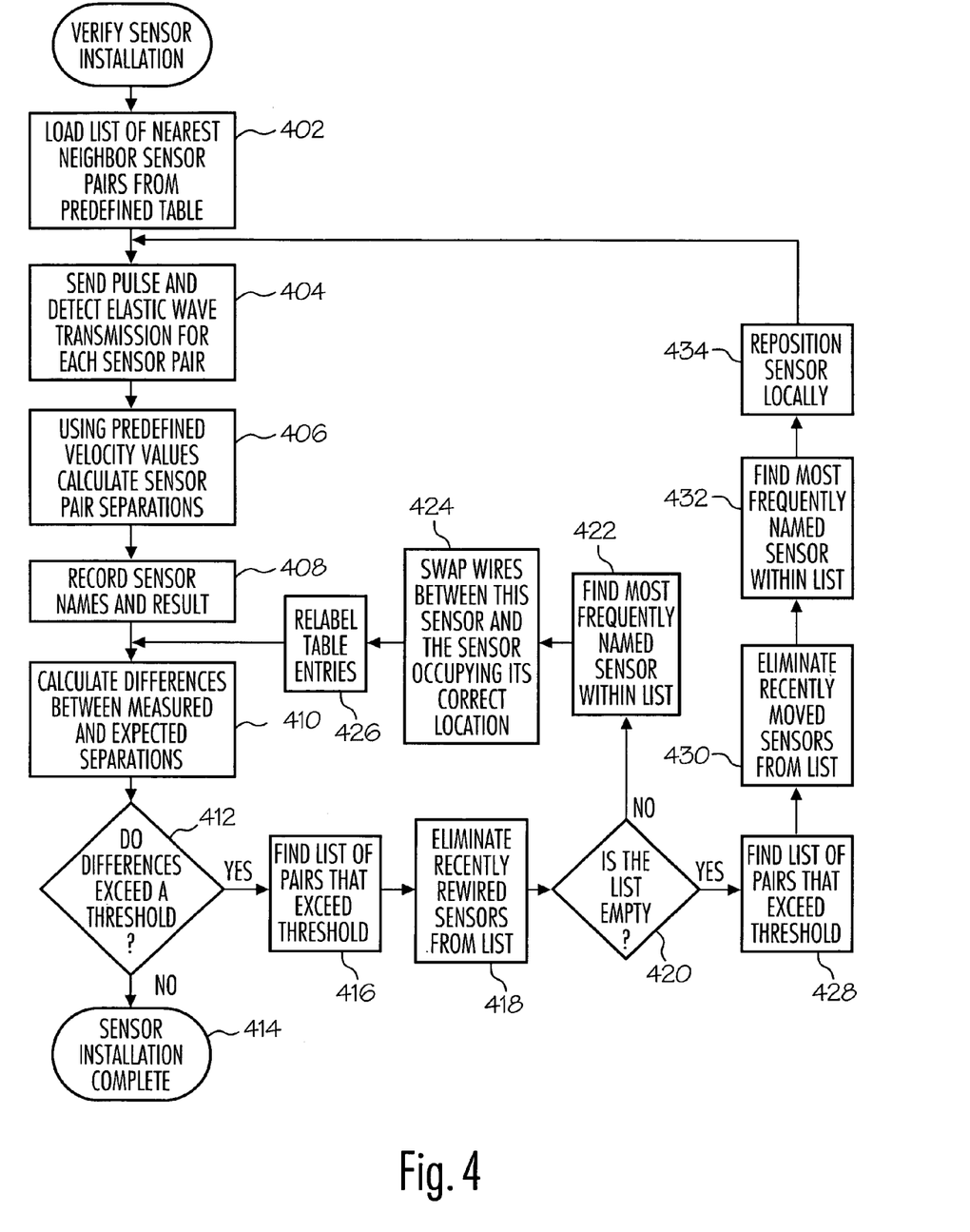
FIG. 4 is a flowchart illustrating a method for determining if sensors are correctly installed in accordance with the teachings of the present invention.
Figure 5:
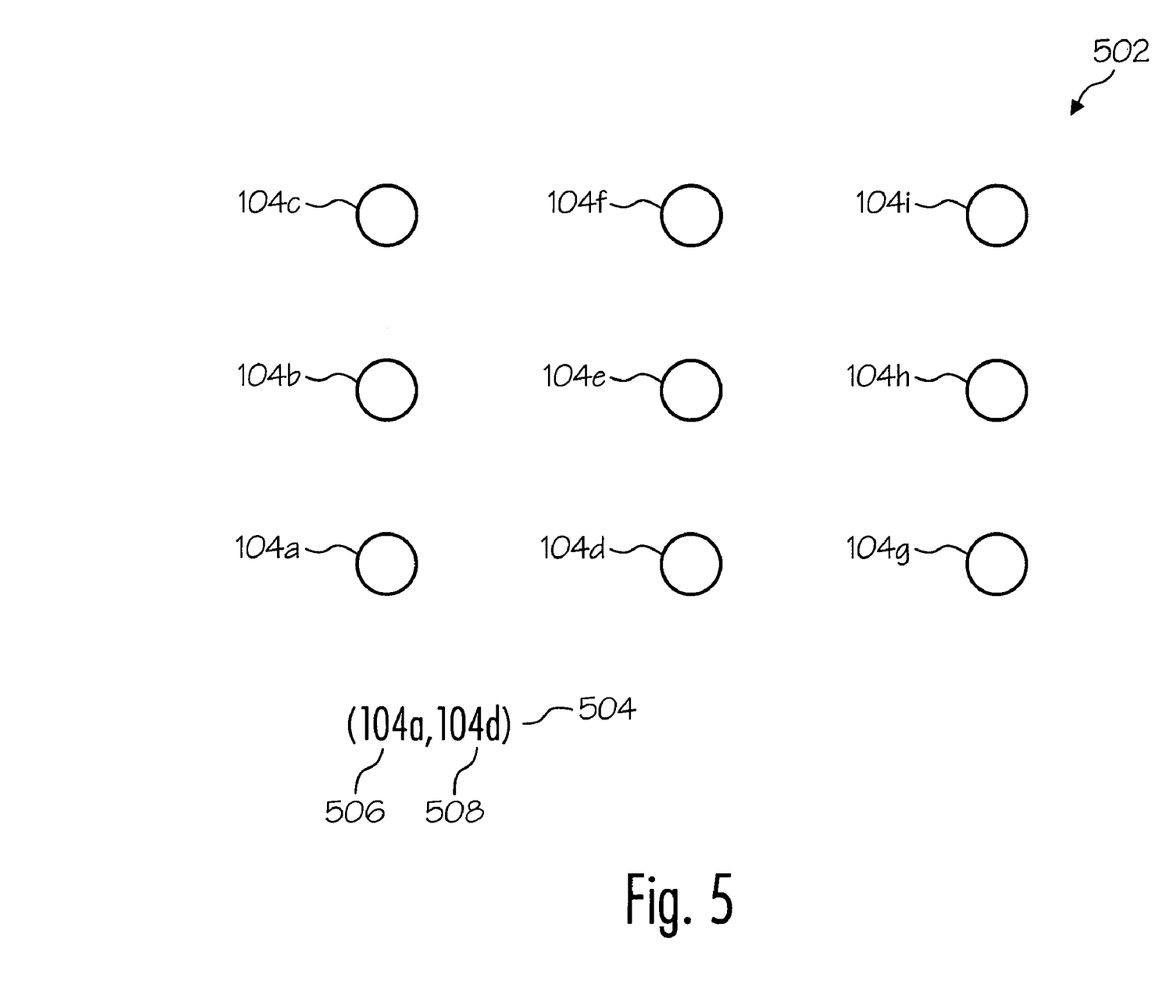
FIG. 5 illustrates an exemplary array of sensors in accordance with the teachings of the present invention.

As discussed previously, human error in installing sensors 104 could result in sensors 104 coupled to the wrong port of the SDC 106, or even to the wrong SDC 106. Also, a sensor could be installed outside an acceptable location by greater than a margin of error allowed for installation variations. An exemplary method to detect such an error is illustrated in FIG. 4. In a first step, step 402, a list of sensor pairs is loaded from a predefined table or listing. With reference to FIG. 5, FIG. 5 illustrates an exemplary array 502 of sensors 104a-104i. The sensor pairs 504, in one embodiment, consist of a selected sensor 506 chosen from amongst all of the sensors 104 paired with a neighbor sensor 508. Neighbor sensors 508 can be sensors directly adjacent to the selected sensor 506 or within a vicinity of the selected sensor 506. In the array 502, sensors 104b, 104d and 104e are neighbor sensors 508 when the selected sensor 506 is sensor 104a. Therefore, in one embodiment, these form sensors pairs (104a, 104b); (104a, 104d); and (104a, 104e). Every sensor 104 in the array 502 can also be paired with its neighboring sensors to form the complete table or listing of sensor pairs 504. Additionally, each sensor pair 504 can also be associated with the distance by which the selected sensor 506 and the neighbor sensors 508 should be separated. This distance can be expressed as an actual distance between sensors or the time it would take a pulse to travel from one sensor 104 to another after accounting for any local variations in the velocity of the waves travel in the structure.

Next, in step 404, each selected sensor 506 is pulsed and the wave transmission is detected at the neighbor sensor 508 for every sensor 104. The result is that for every sensor pair 504, a time value is captured, the time value being the time needed for the wave to propagate from the sending sensor (selected sensor 506) to the receiving sensor (neighbor sensor 508) in the sensor pair 504. This time value is also known as the time of flight. The time value is then multiplied by the local wave velocity propagation value (i.e., the speed at which the wave travels within a particular region of the structure) to obtain a separation value for each sensor pair 504 in step 406. The wave velocity propagation value varies depending on the composition of the structure through which the wave is propagating. The calculated separation values are associated with sensor pairs 504 and are stored in a table or similar structure, in step 408.

Next, in step 410, for each sensor pair 504, the calculated separation distance is compared with a predetermined desired separation distance and a calculated difference is determined. In step 412 it is determined if the difference between the calculated separation distance and the predetermined desired separation distance for each sensor pair 504 is less than some predetermined threshold. If the difference is less than the predetermined threshold for each sensor pair 504, then the sensor installation is complete in step 414 and the method ends.

If the calculated separation distance as determined in step 410, exceeds the threshold for one or more sensor pairs 504, as determined in step 412, in step 416 a listing is made of each of the sensor pairs 504 where the calculated distance exceeded the predetermined threshold in step 416. From the list of sensor pairs 504 determined in step 416, any sensor pairs 504, corresponding to recently rewired sensors are removed from the list, in step 418. Under extreme circumstances of incorrectly installed sensors, the recently repositioned sensor may still show up as incorrectly wired due to the remaining misplaced nearest neighbors. Eliminating the most recently wired sensor from the list eliminates the possibility of attempting to repetitively rewire the same sensor.

After the recently rewired sensors are removed from the list generated in step 416, in step 420, it is determined if the list is now empty. If the list is empty, the list of all sensor pairs 504 that the calculated difference exceeded the threshold, as determined in step 412, is generated in step 428. This is the same list as determined in step 416. From that listing, all sensor pairs 504 corresponding to recently moved sensors are eliminated from the list in step 430.

For all the sensor pairs 504 remaining on the list, the sensor appearing most frequently in the listing from step 428 is identified in step 432. The sensor appearing most often represents an out of position sensor. In step 434, the sensor appearing most often is repositioned manually. In one embodiment, an indication that a sensor needs to be moved can be provided, such as via a display 110. After that, each sensor pair 504 is then checked again at step 404.

If, at step 420, the list of all sensor pairs 504 where the calculated difference exceeded the threshold is not empty, the sensor most frequently found in the list of remaining sensor pairs 504 is determined in step 422. Then, the connection wires of the sensor 104 identified in step 422 and the sensor 104 occupying the position where the sensor identified in step 422 should be located are exchanged in step 424. In one embodiment of the present invention, an indication is provided to the user that wires need to be switched. In step 426, the sensor pairs 504 in the predetermined list of sensor pairs 504 are updated to reflect the changes of step 424. Then, the difference between the predetermined separation values and the calculated separation values is determined again in step 410.

In the method as described in FIG. 4, various actions such as calculating, comparing and the like were discussed. In one embodiment of the present invention, these actions can be carried out using software running on the processor 108 (as well as any necessary components). In another embodiment, at lease some of the actions carried out by the processor 108 can be done at the SDC 106. Indeed, the actions described in FIG. 4 can be accomplished using any number of arrangements of hardware and software functionality as is known to those of ordinary skill in the art. Additionally, although the calculation of the separation value between sensor pairs as seen in steps 402-408, represents a preferred method, any method to the calculate separation value can be used in accordance with the teachings of the present invention.

FIG. 4 illustrates an exemplary method for determining if the installation of the sensors was correctly done. For the best results, sensor location in strucutral health monitoring systems needs to be accurately known in reference to a known coordinate system. Thus, while the exemplary method of FIG. 4 allows a user to determine if sensors are mis-wired or installed outside the allowed location tolerance, a further method is required to accurately locate the sensors and to reference their position in relation to the monitored structure. For example, in a typical aircraft, every location in the aircraft can be referenced to an airplane coordinate system. To accurately access damage in the aircraft, each sensor needs to be located in reference to the coordinate system.

Figure 6:
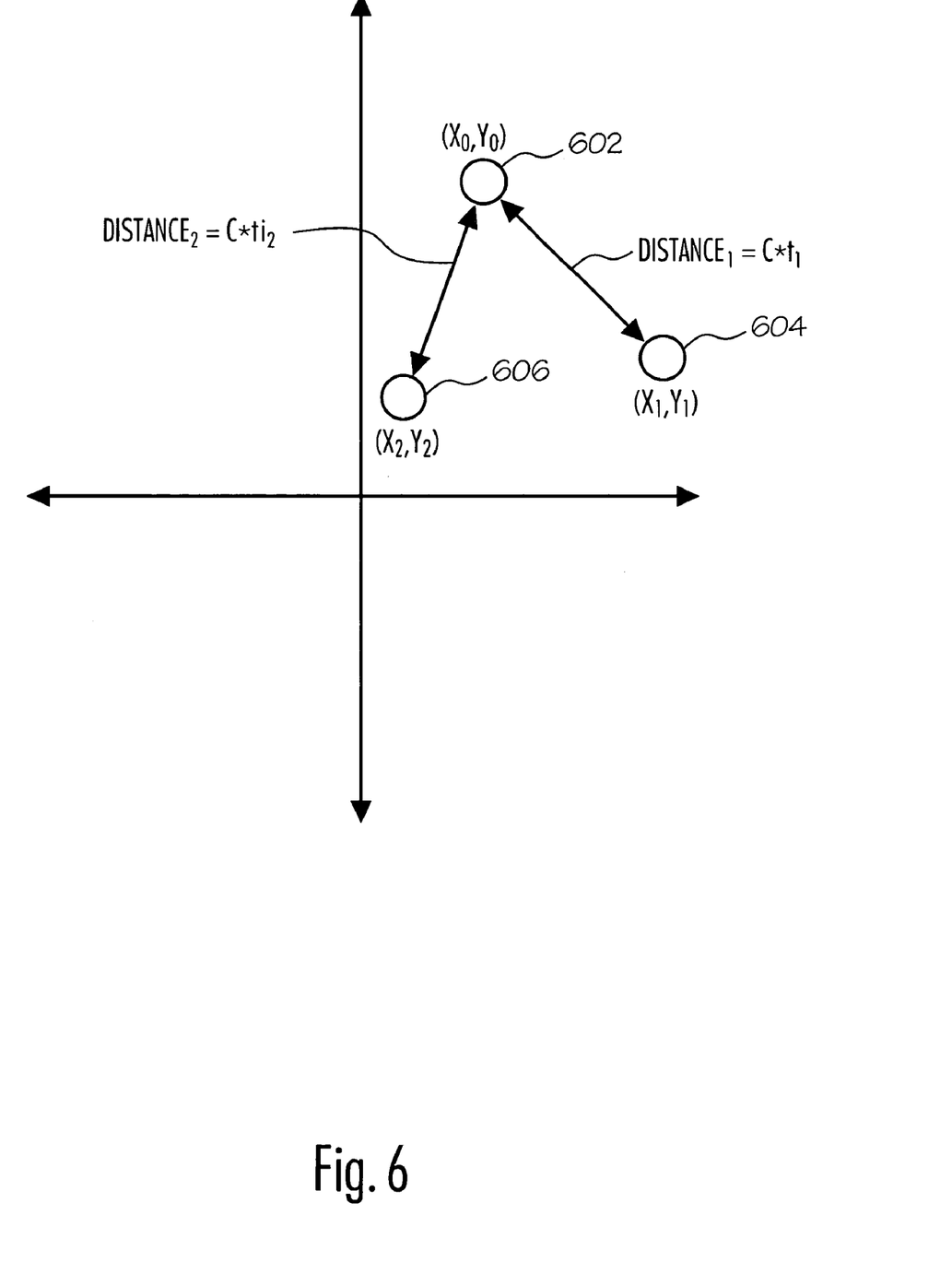
FIG. 6 illustrates the relationship between a sensor of presumed location and sensors of presumed location in accordance with the teachings of the present invention.
Figure 7:
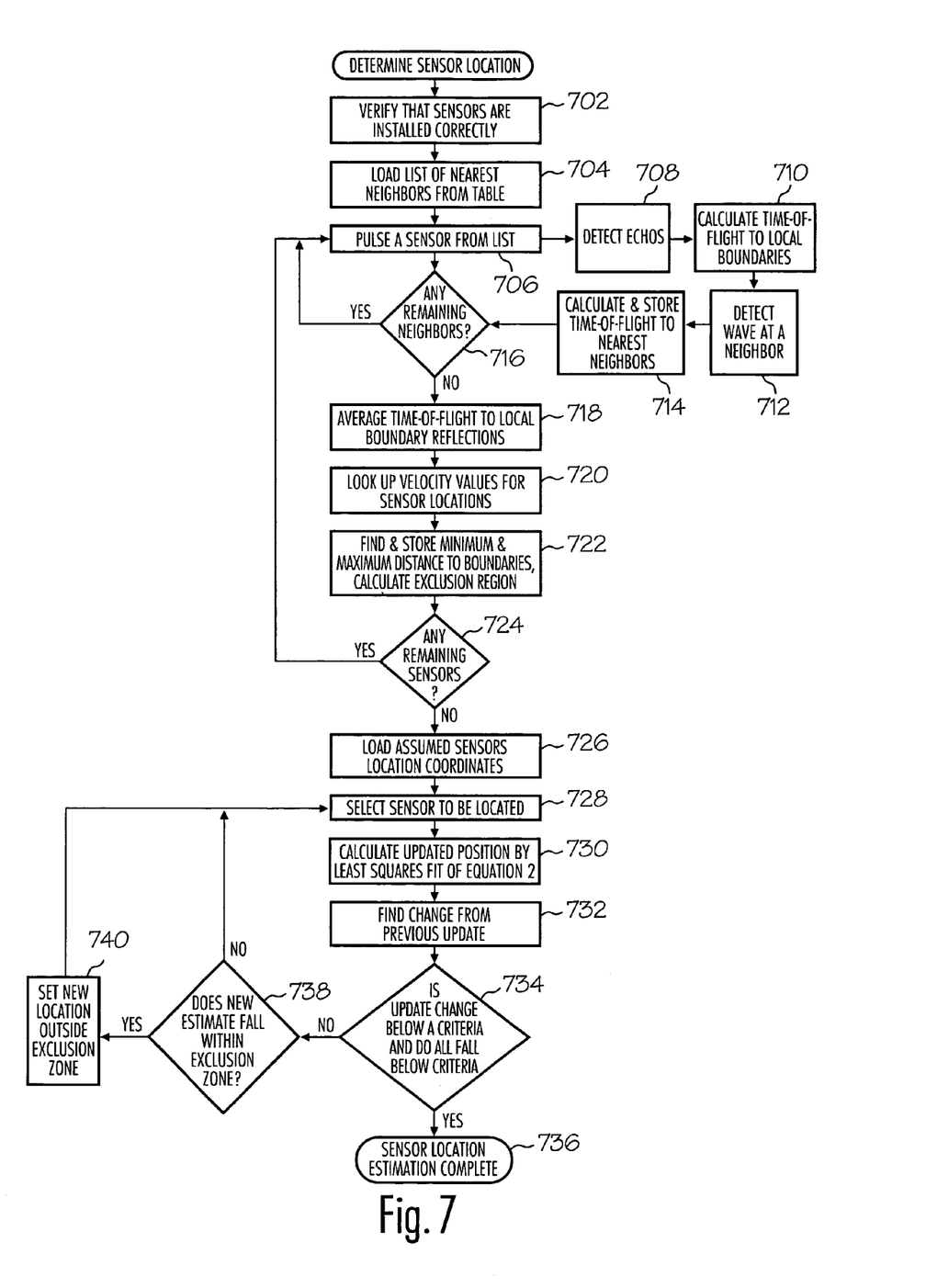
FIG. 7 is a flowchart illustrating a method for determining the location of the sensors in accordance with the teachings of the present invention.

An exemplary method for accurately locating installed sensors is illustrated in conjunction with FIGS. 6-7. In one embodiment of the present invention, the known location of the stringer members 206 and frame members 204, as well as the time-of-flight data from neighboring sensors can be used to determine the locations of one or more sensors 104. FIG. 6 illustrates an unknown sensor 602 that represents a sensor 104 at an unknown location $(x_0, y_0)$. First known sensor 604 and second known sensor 606 represent sensors 104 at a known locations $(x_1, y_1)$ and $(x_2, y_2)$ respectively. By combining the two equations for the distance between the two points a relationship between unknown sensor 602, first known sensor 604 and second known sensor 606 can be expressed as:

$$2x_0(x_2-x_1)+2y_0(y_2-y_1)=2C^2 t_0(\Delta t_1-\Delta t_2)+C^2(\Delta t_1^2-\Delta t_2^2)+(y_2^2-y_1^2)+(x_2^2-x_{12}) \qquad \text{Eqn. 1}$$

where C is the local velocity of the wave in the material, $t_1$ is time for the wave to reach the first known sensor 604, and $t_2$ is time for the wave to reach the second known sensor 606. Here, $t_1$ and $t_2$ have been rewritten in the form $t_1=t_0+\Delta t_1$, and $t_2=t_0+\Delta t_2$, where $t_0$ is the time required for the wave to reach the sensor closest to the unknown sensor 602. This substitution is done to illustrate that the solution can be determined even if only the time-of flight differences, $\Delta t$, between sensors of known location can be measured. In the typical embodiment, the time of flight from the unknown sensor to the known sensor locations is used and the resulting equation is:

$$2x_0(x_j-x_i)+2y_0(y_j-y_i)=C^2(t_i^2-t_j^2)+(y_j^2-y_i^2)+(x_j^2-x_i^2) \qquad \text{Eqn. 2}$$

The indices i and j take on values to indicate nearest neighbor sensors 508 in all possible non-recurring combinations of sensor pairs 504. When three or more nearest neighbors are used Eqn. 2 results in an overdetermined set of equations (a set of equations with more equations than unknown variables) for which the two unknown values; $(x_0, y_0)$ can be solved, typically by using the well known mathematical method of least square fit.

As illustrated in FIG. 2, the sensors 104 are placed in areas that are bounded, in most cases, by stringer members 206 and frame members 204. As discussed previously, the locations of these structural parts are known and can be referenced to an aircraft coordinate system. To improve the accuracy of locating a sensor, the time of flight required for a pulse to reflect from each of the structural members can be determined. This data provides additional constraints for determining the location of the sensors. In one embodiment, the equations derived from the locations of the stringer members 206 and frame members 204 can be can be used in the least squares fit and weighted according to the quality of the data. In this embodiment, the solutions can be determined using the least square fit techniques of constrained optimization.

FIG. 7 is a flowchart of an exemplary method for estimating the location of a sensor 104. As discussed previously, although sensors 104 are placed such that they are located within the acceptable installation criteria, more precise location is needed for accurate damage assessment. In a first step, step 702, it is determined if the sensors 104 are correctly installed. An exemplary method for checking the installation of the sensor is illustrated in conjunction with FIG. 4.

Next, in step 704, a list of sensor pairs 504 is either generated or retrieved from a database or memory. As before, sensor pairs 504 comprise a selected sensor 506 and a neighbor sensor 508, the neighbor sensor 508 adjacent to or in the vicinity of the selected sensor 506.

Next, in step 706, a sensor 104 is chosen as the selected sensor 506 from the list of sensor 104 and the selected sensor 506 is pulsed to produce an elastic wave in the material. The waves' reflections off the local boundaries are detected, in step 708, at the selected sensor 506 that initiated the pulse. The local boundaries, in one embodiment, are the stringer members 206 and the frame members 204 as illustrated in FIG. 2. In step 710, the time of flight to the local boundaries is calculated. In one embodiment, the time it takes a pulse to be generated, reflected against a boundary and returned to the sensor 104 can be used to find the time of flight to the boundaries.

Additionally, the transmitted wave can also be detected at each neighbor sensor 508 (step 712) to determine the time it takes for the pulsed wave to travel from the transmitting sensor (selected sensor 506) to one of the neighbor sensors 508. The time it takes the wave to travel from the selected sensor 506 to the neighbor sensor 508 is stored in step 714. Steps 706 through 714 are repeated for each sensor 104 that neighbor the selected sensor 506.

Then, in step 718, the time of flight to the local boundaries for the selected sensor 506 are averaged. The velocity value for waves in the material is determined next in step 720. The velocity value for a wave varies depending on the material, structure and the elastic wave employed. The requisite velocity value for the local; region and material conditions can be stored in a lookup table or similar structure for use in a computer implemented method. In step 722, the minimum and maximum distances of the selected sensor 506 to local boundaries are calculated and stored. From the different signals received, a minimum distance from the selected sensor 506 to these boundaries can be calculated using the earliest echo reflected from the boundaries. A maximum distance to the boundaries can be calculated using the appropriate echo reflected later in time. These minimum and maximum distances from the local boundaries can be used to construct a region where the sensor must physically be located and exclusion regions where the sensors can not be located. In step 724 it is determined if all sensors 104 have been pulsed. If not, then steps 706-722 are repeated for each sensor with each sensor being the selected sensor eventually.

After all sensor pairs have been evaluated in steps 706-724, in step 726 the assumed locations of the sensors 104 are loaded from a database, table or the like. Initially, the assumed locations are the positions where the sensors 104 would be if ideally placed. Typically, the sensor locations are referenced based on a coordinate system that uniquely maps each location in the system. In an avionics embodiment, locations are referenced to an airplane coordinate system. The assumed location provides an initial location to use to compare calculated locations.

Next, one of the sensors 104 in the collection of sensors 104 is selected for locating, in step 728. In step 730 a least square fit calculation using the time of flight between the sensor and its neighbors, as well as, optionally, time of flight data between the sensor and the boundaries are used to determine a calculated location. Eqn. 2 is an exemplary equation that can be used to determine the calculated location. In step 732, the updated calculated location for the sensor is compared with the assumed location for the sensor to determine a calculated change.

In step 734, the calculated change is compared to a predetermined change criteria or threshold. If the calculated change is less than the change criteria, the new estimated sensor location for the sensor is at the calculated location. Additionally, in one embodiment, the calculated location replaces the assumed location for the sensor in the table of assumed locations that was determined in step 706. In this manner, the table or other collection of location sites is updated with a new calculated location each time sensors are evaluated. Step 734 also determines if the calculated change for all of the sensors in the system fall below the change criteria. This is done after a calculated location for each sensor has been determined. Prior to that occurrence, after a sensor is evaluated, a next sensor is chosen for evaluation. Once the calculated change for each sensor falls below the change criteria, the method is complete at step 736.

On the other hand, if the calculated change exceeds the change criteria, the method proceeds to step 738 where it is determined if the updated calculated location falls within the exclusion region as determined in step 722. If the updated calculated location falls outside the exclusion region, the sensor's estimated location is the calculated location. Also, this calculated location, in one embodiment, replaces the assumed location in the table of assumed location discussed in step 726. Then, any remaining sensors are evaluated, starting at step 728.

In step 740, if the updated calculated location falls within the exclusion region, the sensor is located outside the exclusion region and as close to the updated calculated location as possible. This is the calculated location for the sensor. The calculated location can then, in one embodiment of the present invention, replace the assume location of the sensor in the table discussed in conjunction with step 726. Then, any remaining sensors are evaluated, starting at step 728.

As discussed in conjunction with step 734, the process of calculating new calculated locations continue until the calculated change for every sensor falls below the chosen criteria. When this occurs, all sensors are located with reference to the coordinate system, such as an airplane coordinate system.

In the method as described in FIG. 7, various actions such as calculating, comparing and the like were discussed. In one embodiment of the present invention, these actions are carried out using software running on the processor 108 (as well as any necessary components). In another embodiment, at lease some of the actions carried out by the processor 108 can be done at the SDC 106. Indeed, the actions described in FIG. 7 can be accomplished using any number of arrangements of hardware and software functionality as is known to those of ordinary skill in the art. Additionally, calculation of time of flight between sensors and the determination of exclusion regions, as outlined in steps 702-724, represents a preferred method; any method to calculate the time of flight between sensors and exclusion regions are within the teachings of the present invention.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. A method for locating a plurality of sensors in relation to a fixed coordinate system, the method comprising:
   retrieving a list of sensor pairs derived from the plurality of sensors, each sensor pair comprising a selected sensor and a neighbor sensor;
   for each selected sensor, determining a sensor time of flight between the selected sensor and each neighbor sensor;
   for each selected sensor, determining a boundary time of flight between the selected sensor and a plurality of local boundaries of the selected sensor and using the boundary time of flight to determine local exclusion regions where the selected sensor can not be located with respect to the local boundaries;
   for each selected sensor, calculating an updated position using the boundary time of flight between the boundaries and the sensor time of flight between each sensor pair;
   for each selected sensor, comparing the updated position with a previous position; and
   for each selected sensor, if the updated position is within a predetermined threshold of the previous position, estimating the selected sensor's location at the updated position.

2. The method of claim 1 further comprising setting the location of the selected sensor at the updated position if the updated position exceeds the previous position by the predetermined threshold and is outside the local exclusion region.

3. The method of claim 2 further comprising determining a modified updated position for the selected sensor such that the modified updated position is the closest position to the updated location that is not within the exclusion region, if the updated position is within the exclusion region and the updated location exceeds the previous position by the predetermined threshold.

4. The method of claim 3 wherein all sensors are correctly located when each of the plurality of sensors are within the predetermined threshold of the previous position.

5. A structural health monitoring system comprising:
- a plurality of sensors installed in a structure having local boundaries for each sensor; and
- a processor coupled to each of the sensors, the processor configured to determine a sensor time of flight between the sensors and a boundary time of flight between each sensor and the sensor's local boundaries, the processor further configured to calculate an updated location for each of the sensors from the sensor time of flight and the boundary time of flight.

6. The system of claim 5 wherein the processor is further configured to compare the updated location for each sensor with an expected location and determine if a difference between the updated location and the expected location is within a predetermined threshold.

7. The system of claim 6 wherein the processor is further configured to accept the updated location if the updated location does not exceed the expected location by more than a predetermined threshold.

8. The system of claim 7 wherein the processor is further configured to accept the updated location if the updated location exceeds the predetermined threshold but the updated location is outside an exclusion region determined by the boundary time of flight.

9. The system of claim 8 wherein the processor is further configured to determine a new updated location if the difference between the updated location and the expected location exceeds a predetermined margin and the updated location is in the exclusion region, the new updated location set as a location outside the exclusion region and closest to the updated position.

10. The system of claim 9 wherein the processor is configured to continue to calculate the updated position of each sensor until the updated position is within a predetermined margin of error of the expected location.

* * * * *